(12) United States Patent  (10) Patent No.: US 8,814,811 B2
Scholten et al.  (45) Date of Patent: Aug. 26, 2014

(54) FALL DETECTION ALGORITHM UTILIZING A THREE-AXIS ACCELEROMETER

(75) Inventors: Patrick Scholten, Lettele (NL); Harry Bernardus Antonius Kerver, Duiven (NL)

(73) Assignee: Medtronic, Inc., Minneapolis, MN (US)

( * ) Notice: Subject to any disclaimer, the term of this patent is extended or adjusted under 35 U.S.C. 154(b) by 1079 days.

(21) Appl. No.: 12/126,084

(22) Filed: May 23, 2008

(65) Prior Publication Data

US 2009/0292227 A1 Nov. 26, 2009

(51) Int. Cl.
*A61B 5/103* (2006.01)

(52) U.S. Cl.
USPC ............................................. 600/595; 607/62

(58) Field of Classification Search
USPC ............ 600/595, 587, 552, 553; 607/1–6, 48, 607/49, 62, 63
See application file for complete search history.

(56) References Cited

U.S. PATENT DOCUMENTS

| 5,233,984 | A | | 8/1993 | Thompson |
| 5,354,317 | A | | 10/1994 | Alt |
| 5,464,434 | A | | 11/1995 | Alt |
| 5,472,453 | A | | 12/1995 | Alt |
| 5,593,431 | A | | 1/1997 | Sheldon |
| 5,701,894 | A | * | 12/1997 | Cherry et al. ................. 600/300 |
| 5,865,760 | A | | 2/1999 | Lidman et al. |
| 5,987,352 | A | | 11/1999 | Klein et al. |
| 6,044,297 | A | | 3/2000 | Sheldon et al. |
| 6,104,949 | A | | 8/2000 | Pitts et al. |
| 7,181,281 | B1 | | 2/2007 | Kroll |
| 2001/0004234 | A1 | | 6/2001 | Petelenz et al. |
| 2005/0148897 | A1 | | 7/2005 | Cho et al. |
| 2007/0146145 | A1 | | 6/2007 | Lehrman et al. |

FOREIGN PATENT DOCUMENTS

| WO | WO2007148246 | * | 5/2007 |
| WO | 2007148246 | | 12/2007 |

OTHER PUBLICATIONS

Hwang et al. "Development of Novel Algorithm and Real-time Monitoring Ambulatory System Using Bluetooth Module for Fall Detection in the Elderly" IEEE Sep. 2004, pp. 2204-2207.*
International Search Report, PCT/US2009/043762, 4 pages.

* cited by examiner

*Primary Examiner* — Max Hindenburg
*Assistant Examiner* — Renee Danega
(74) *Attorney, Agent, or Firm* — Michael J. Ostrom; Stephen W. Bauer

(57) ABSTRACT

A three-axis accelerometer signal is used in a medical device for detecting that a patient has fallen. The accelerometer signal is sampled at a low sampling rate for determining a patient position. The accelerometer signal is sampled at a high sampling rate for determining an acceleration magnitude in response to determining the patient position. The patient position and acceleration magnitude are used to detect that a patient has fallen.

9 Claims, 6 Drawing Sheets

FALL DETECTION ALGORITHM UTILIZING A THREE-AXIS ACCELEROMETER

TECHNICAL FIELD

The disclosure relates generally to implantable medical devices and, in particular, to an apparatus and method for detecting that a patient has fallen.

BACKGROUND

In implantable medical devices (IMDs) used for monitoring for syncope, patients are often provided with a patient activator to use when the patient feels symptomatic for triggering physiological data storage by the implanted device. Physiological data may include subcutaneous ECG signal data as well as other physiological signals depending on the capabilities of the IMD. In some circumstances, the patient may experience syncope, fall down and be unable to get to or use the patient activator in order to trigger the data storage. It is desirable to store signals sensed by the implanted device leading up to and during the syncope episode causing the fall.

DETAILED DESCRIPTION

Figure 1:
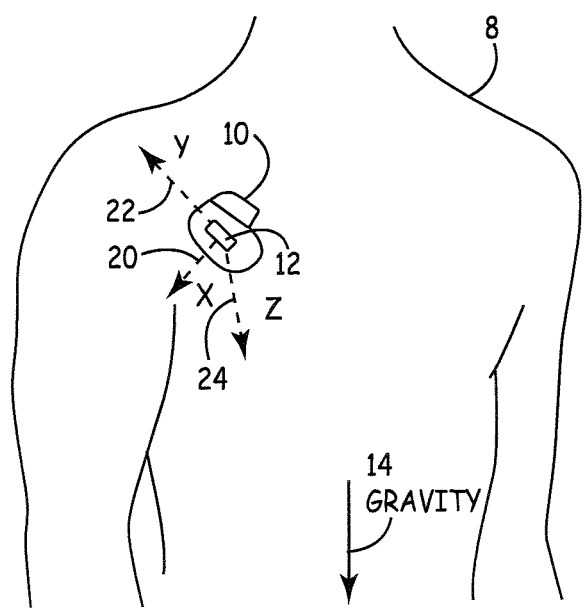
FIG. 1 is a schematic diagram of an IMD implanted in a patient and including a three-axis accelerometer for use in detecting if a patient has fallen.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a schematic diagram of an IMD 10 implanted in a patient 8 and including a three-axis accelerometer 12 for use in detecting if a patient has fallen. As used herein, the terminology "has fallen" is distinguished from "is falling" in that if the patient "has fallen" the patient has already made impact with a surface such as the ground or floor. When a patient "is falling", the patient is still in the process of falling from an upright position and has not yet made impact with a surface. In other words, the patient that "is falling" is still moving through the air and has not yet struck the ground or another surface; the patient that "has fallen" has made impact with a surface and is in a non-upright position subsequent to the impact.

An "upright position" as used herein generally refers to a position from which a patient can fall downward in response to gravity, particularly during syncope, but is not already in the act of falling. An "upright position" is typically a position in which at least the patient's upper body is substantially aligned with gravity. Examples of upright positions include, but are not limited to, standing, walking, and running. Upright positions may also include sitting positions. A "non-upright position" as used herein generally refers to a position from which a patient would not fall downward. As such a "non-upright position" is typically a position in which at least the patient's upper body is not substantially aligned with gravity. Examples of non-upright positions include, but are not limited to, prone, supine, reclining and side-lying positions.

The orientation of the three-axis accelerometer 12 with respect to gravity 14 when the patient is in an upright position will vary between patients since the implanted orientation of the IMD 10 with respect to gravity 14 will vary. In one embodiment, the three-axis accelerometer 12 includes three orthogonally arranged one-axis accelerometers each producing a respective signal corresponding to acceleration in an x-direction 20, a y-direction 22, or a z-direction 24. In an alternative embodiment, three single-axis accelerometers may be arranged in a non-orthogonal configuration wherein each accelerometer is positioned along a unique plane relative to the other two accelerometers. A three-axis accelerometer may alternatively include two two-axis accelerometers, for example in an orthogonal arrangement or a non-orthogonal arrangement wherein the two accelerometers are arranged in unique planes relative to each other. A three-dimensional accelerometer signal may also be obtained from any combination of a one-axis and a two-axis accelerometer in which the one-axis accelerometer is positioned along a plane of sensitivity unique to the two-axis accelerometer planes of sensitivity, the plane of sensitivity being the plane along which accelerations cause the accelerometer to generate an electrical signal.

Figure 2:
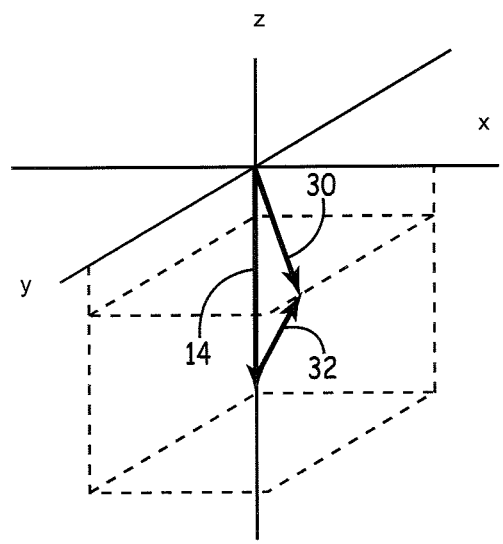
FIG. 2 is a three-dimensional diagram of an output of a three-axis accelerometer with respect to gravity.

FIG. 2 is a three-dimensional diagram of an output of a three-axis accelerometer with respect to gravity 14. An output vector 30 of the three-axis accelerometer is a summation of gravity 14 and a movement vector 32 defined by the acceleration of the accelerometer in the three x, y and z directions shown in FIG. 1. The magnitude of the output vector 30 can be computed as a mathematical combination of the x, y and z components. In one embodiment, the magnitude of output vector 30 is computed as a Euclidean norm, i.e., the square root of the sum of squares of the orthogonal vectors:

$$\|v\| = (x^2 + y^2 + z^2)^{1/2}$$

In general, the magnitude of the output vector is 1.0 g (9.8 m/s$^2$) if there is no acceleration/deceleration of the three-axis accelerometer (movement vector 32 is zero).

Figure 3:
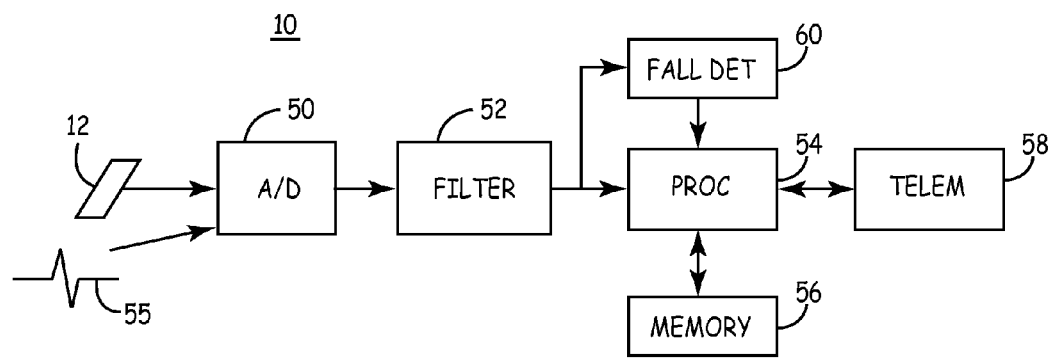
FIG. 3 is a functional block diagram of IMD 10 according to one embodiment.

FIG. 3 is a functional block diagram of IMD 10 according to one embodiment. IMD 10 includes three-axis accelerometer 12 coupled to an analog-to-digital (A/D) converter 50 for sampling the accelerometer signal for example at 256 samples per second. The term "3D accelerometer signal" as used to herein refers to the signal generated by any of the implementations of a three-axis accelerometer as described above. The 3D accelerometer signal thus includes at least three acceleration signals corresponding to three different axes defined by the planes/axes of sensitivity of the accelerometers. A filter 52 receives and filters the sampled signal and provides the signals to a processor 54. In some embodiments, filter 52 is implemented as an analog filter for filtering analog signals before digital conversion by A/D converter 50. Processor 54 performs algorithms using the digitized filtered 3D signal for detecting if the patient has fallen. Alternatively, a dedicated fall detection module 60 may be implemented using any combination of hardware, firmware and software for detecting if the patient has fallen using the 3D accelerometer signal and according to methods described herein.

Filtering of the accelerometer signal may include low pass filtering, e.g. a 0.5 Hz first order low pass Butterworth filter, to remove signals corresponding to activity of the patient. The low pass filtered signal is used to compute a reference vector corresponding to an upright position and to compute current position vectors as will be described herein. Filtering of the accelerometer signal may also include band pass filtering, e.g. using a 1 Hz to 50 Hz first order band pass Butterworth filter to remove the static component of the 3D accelerometer signal, which includes the effect of gravity. The band pass filtered signal is used to detect high magnitude acceleration signals that occur when a patient has fallen, particularly when the patient strikes the ground or other surface.

The processor 54, either alone or in combination with fall detection module 60, detects that the patient has fallen according to methods described herein and initiates storage of physiological data in memory 56. In one embodiment, IMD 10 is configured to sense an ECG signal 55 of the patient, which generally also undergoes digital sampling and filtering through A/D converter 50 and filter 52, for use in diagnosing cardiac-related syncope. Sampling rates and filtering of one or more ECG signals may be defined differently than sampling and filtering of the accelerometer signal. A/D converter 50 and filter 52 shown as functional blocks in FIG. 3 may therefore include more than one A/D converter and filter for performing all of the digitizing and filtering functions needed to acquire and store physiological signals other than the 3D accelerometer signal according to a specific implementations.

Upon detecting that the patient has fallen, the processor 54 triggers long-term storage of the ECG signal in memory 56 during an interval of time defined relative to the fall detection. Prior to detecting the fall, ECG signal data is stored in a temporary, looping manner in memory 56. Once the data storage triggering event occurs, the temporary data is stored in long-term memory. Data stored in long-term memory may remain in memory 56 until it has been uplinked from IMD 10 to another device via telemetry module 58, after which long-term memory data may be cleared. Triggered physiological data storage in a looping memory format is generally disclosed in U.S. Pat. No. 5,987,352, (Klein, et al.), hereby incorporated herein by reference in its entirety.

While FIGS. 1 and 3 have been described relating to an IMD, it is recognized that embodiments of the present invention also include external monitoring devices which include a three-axis accelerometer, such as an external ECG monitor that is worn by a patient. In this case, telemetry module 58 may be a wireless or hardwired communication module for transferring data to a computer or other device for review by a clinician.

Figure 4:
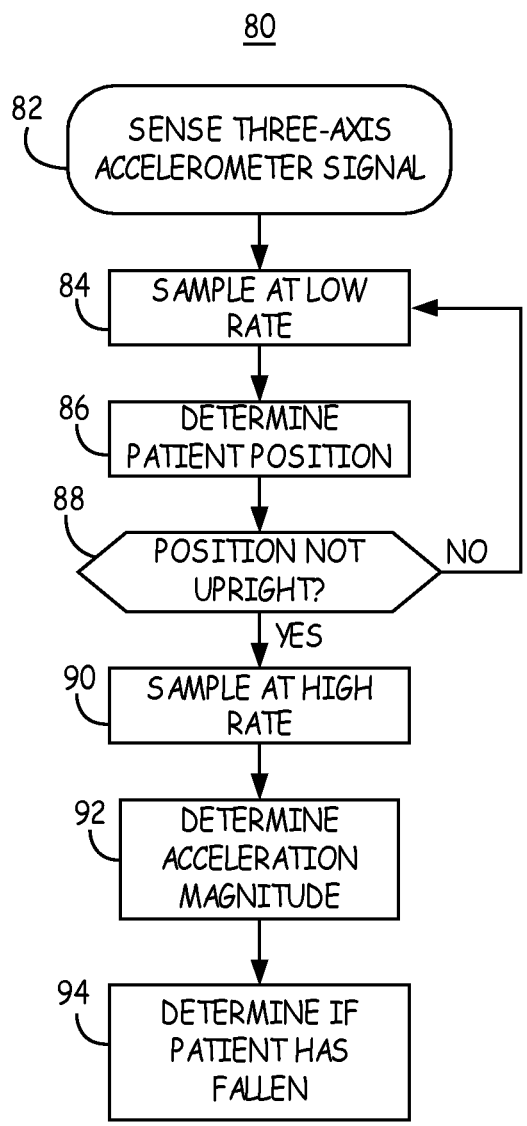
FIG. 4 is a flow chart of one method for detecting if a patient has fallen.

FIG. 4 is a flow chart of one method for detecting if a patient has fallen. Flow chart 80 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern implantable device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 82, a three-axis accelerometer signal is sensed for ambulatory monitoring of a patient for detecting that the patient has fallen. At block 84, the 3D accelerometer signal is sampled at a low rate. The low sample rate is selected to allow detection of a patient fall within a desired time of the patient fall but minimize processing power required for detecting the fall. For example, the sampling rate may be once per second to allow detection that the patient has fallen within 1 to 2 seconds of the patient fall. The low rate sampled signal is used to monitor the patient's position at block 86 to detect when the patient is not in an upright position as indicated at block 88. Methods for detecting when the patient is not in an upright position will be described in more detail below. The low sample rate analysis for determining the patient position may be performed continuously without excessive processing power burden on the IMD.

When the patient is detected as not being in an upright position at block 88, based on the low sample rate analysis, a 3D accelerometer signal sampled at a high rate at block 90 is analyzed at block 92. In one embodiment, high rate sampling is occurring continuously at block 90 with the high rate sampled signal stored in a looping manner in a temporary memory buffer contemporaneously with the low rate sampling such that the high rate sampled signal is available for analysis at block 92 upon detecting that the patient is not upright at block 88. In other embodiments, the determination at block 88 may trigger the onset of high rate sampling of the 3D accelerometer signal.

A high sampling rate may be 256 samples per second in one illustrative embodiment. High magnitude high frequency acceleration signals occur when a patient strikes the ground or floor due to a fall. As such, a high sample rate signal analysis is performed at block 92 after detecting that a patient is not in an upright position to determine if the patient experienced high magnitude accelerations within a short time, for example 1 to 2 seconds, of detecting that the patient is not in an upright position. At block 92, the magnitudes of signal samples obtained at the high sample rate are determined. A determination if the patient has fallen is made at block 94 based on the acceleration magnitudes. The determination at block 94 may further include additional analysis of the low rate sampled signal as will be described in detail below.

As such, methods described herein for detecting if a patient has fallen generally include first detecting if a patient position is not an upright position during analysis performed on the 3D accelerometer signal sampled at a low sample rate. Determination that the patient is not in an upright position then triggers an analysis of the magnitude of 3D accelerometer signal samples obtained using a high sampling rate. This low sample rate signal analysis may run continuously without high current consumption from the IMD power supply since the processing power is minimized. Higher processing power for analyzing the high sample rate signal is only required after determining that the patient is not in an upright position.

It is noted that the determination at block 88 is not necessarily equivalent to determining that the patient is in a non-upright position. Since the patient may be in the process of falling at block 88 the patient position may be somewhere intermediate a defined "upright position" and a defined "non-upright position". As such, the determination made at block 88 relates to determining whether the patient's position meets criteria for detecting an upright position; the patient's position may or may not meet criteria for detecting a non-upright position.

Figure 5:
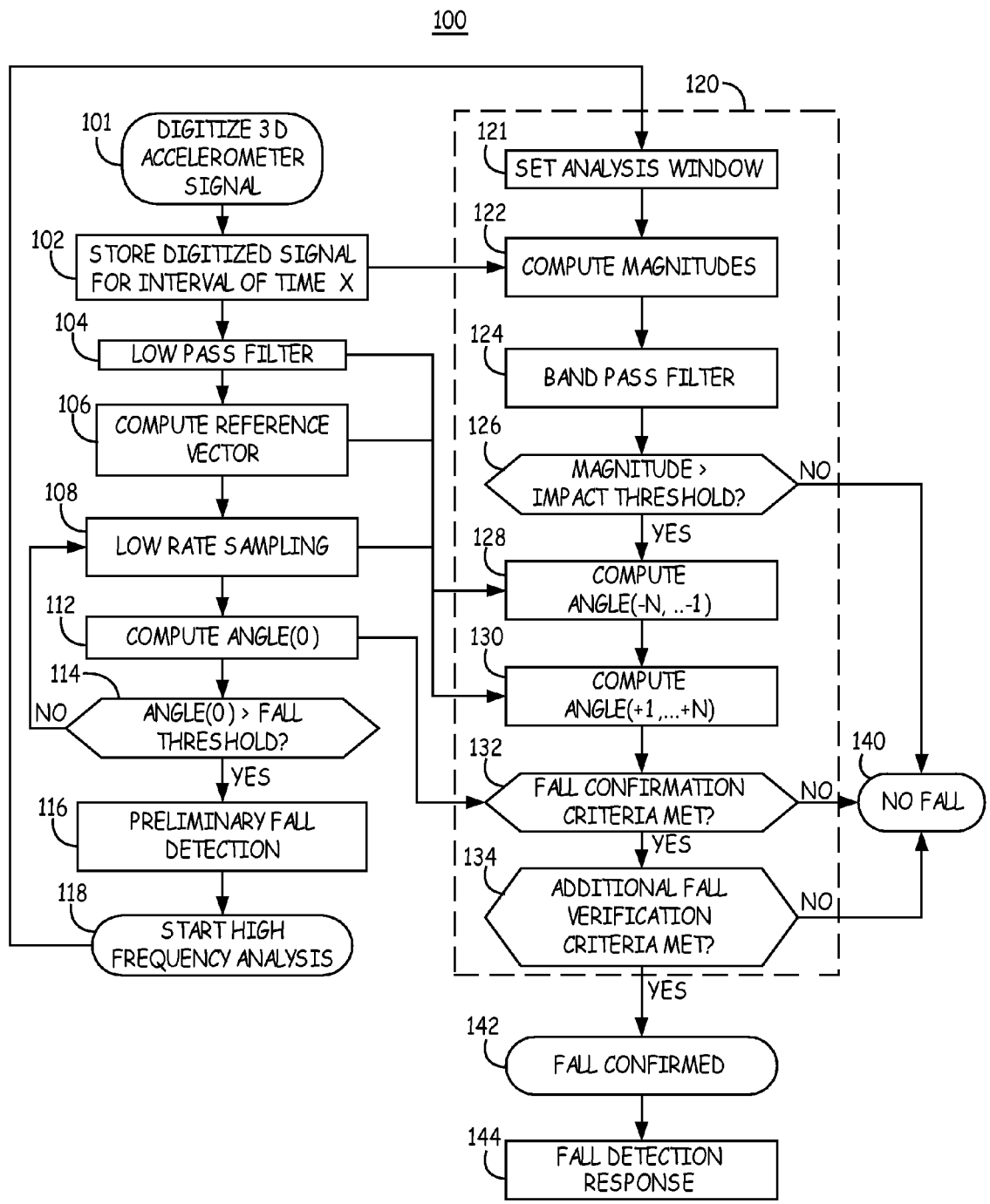
FIG. 5 is a flow chart of a method for detecting if a patient has fallen according to one embodiment.

FIG. 5 is a flow chart 100 of a method for detecting if a patient has fallen according to one embodiment of the invention. At block 101, the 3D accelerometer signal is digitized, for example using a sampling rate of 256 samples per second. The digitized signal is stored at block 102 in temporary memory in a looping manner for an interval of time X. The interval of time X may correspond or at least includes an analysis window as will be described in detail below. Looping storage of the digitized signal may be continuous as long as monitoring for a patient fall is enabled. As will be described below, high sample rate signal data stored at block 102 is only utilized after making a preliminary fall detection based on an analysis of the accelerometer signal sampled at a low sample rate.

The digitized signal is low pass filtered at block 104, for example using a 0.5 Hz low pass filter. The digitized, filtered signal is used to compute a reference vector at block 106. The reference vector corresponds to the three-axis accelerometer output when the patient is known to be in an upright position (e.g., standing or walking). Computation of the reference vector may be performed in an automatic or semi-automatic procedure. The patient may be asked to assume and maintain an upright position or a command may be transmitted to the IMD indicating the patient is in a stable upright position and that the reference vector computation should be performed. Once the reference vector is determined, it is stored in memory for use during ambulatory monitoring, until it is replaced by a new reference vector.

During ambulatory monitoring, the 3D accelerometer signal is initially monitored using a low sample rate signal analysis performed at blocks 108 through 116. The low sample rate signal analysis evaluates the low frequency component of the 3D accelerometer signal for making a preliminary fall detection. Accordingly, at block 108, the digitized, low pass filtered 3D accelerometer signal is sampled at a low rate, for example 1 sample per second. This low sampling rate allows the IMD to check for a positional change relative to the reference vector on a low frequency basis for fall monitoring.

The low sampling rate may be greater than or less than 1 sample per second in various embodiments. Fall detection will generally not require more frequent checks of the current patient position relative to the reference vector than, for example, about once per second, and this low rate analysis of patient position minimizes power consumption needed for processing and analyzing the 3D accelerometer signal. The time duration of the looping temporary memory storage of the digitized signal at block 102 may be taken into account when selecting the low sampling rate. The low sampling rate may be selected to sample the digitized signal sooner than the looping temporary memory starts overwriting data. It is recognized that the reference vector computed at block 106 may alternatively be computed using the low sampling rate signal data obtained at block 108 rather than directly from the digitized data stored at block 102.

Using a 1 sample per second sampling rate, a current position vector, v(0), is available from the 3D accelerometer signal every second. An angle $\Theta(0)$ between the current position vector v(0) and the reference vector v(ref) is computed at block 112, and is referred to in FIG. 5 as angle(0).

The angle $\Theta(0)$ may be computed according to the following equation {1}, which can be referred to as the "inproduct":

$$\Theta(0)=\arccos\{(v(0)\cdot v(\text{ref}))/(\|v(0)\|*\|v(\text{ref})\|)\}. \quad \{1\}$$

The above computation may be implemented using any combination of hardware, software and firmware. By low pass filtering the sampled signal at block 104, the contribution of patient activity to the accelerometer signal is largely removed such that the output will have a magnitude close to 1 g. The reference vector will also have a magnitude close to 1 g. As such, the denominator of equation {1} approaches 1 thereby simplifying the computation that needs to be performed by the processor. The angle $\Theta(0)$ may be estimated as:

$$\Theta(0)=\arccos\{x(0)x(\text{ref})+y(0)y(\text{ref})+z(0)z(\text{ref})\}. \quad \{2\}$$

At block 114, the computed angle is compared to a fall threshold angle. The fall threshold angle may be any angle selected to indicate that the patient's position has deviated from the upright position (the reference vector) to a point that may correspond to a falling or a fallen position. As such, the fall threshold angle may correspond to an angle at which the patient is still in the act of falling; the patient is no longer upright but is not yet in a non-upright position. In alternative embodiments a fall threshold may correspond to an angle at which the patient is in a non-upright position. In one embodiment, the threshold angle is approximately 45 degrees, but may be selected, for example, to be anywhere between and including approximately 30 degrees and approximately 60 degrees. If the computed angle $\Theta(0)$ exceeds the fall threshold angle, a preliminary fall detection is made at block 116. The threshold angle may change over time as the IMD may migrate and/or rotate with respect to the gravitational vector over time. As such, the threshold angle may be programmable and updatable.

In alternative embodiments, the inverse cosine calculation in equation {1} may be omitted by estimating the cosine of angle $\Theta(0)$, as shown in equation {3}:

$$\cos(\Theta)(0))=\{x(0)x(\text{ref})+y(0)y(\text{ref})+z(0)z(\text{ref})\} \quad \{3\}$$

Computation of the cosine of angle $\Theta(0)$ is less complex than computation of angle $\Theta(0)$ which requires the "arccos" operation. In this case, the calculated cosine of angle $\Theta(0)$ is compared to the cosine of the fall threshold angle for detecting a change in patient position indicative of a fall. The cosine of the threshold angle only has to be calculated once, and is then used as a threshold value for comparison.

The preliminary fall detection made at block 116 indicates that the patient's current position deviates from an upright position by at least the threshold angle. However this deviation may be associated with a mere change in patient position. Additional analysis is performed to determine if other fall detection criteria are satisfied, which indicate that the patient's current position resulting in a fall threshold crossing is indeed associated a patient fall. The preliminary fall detection made at block 116 triggers an analysis of the high frequency components of the 3D accelerometer signal as indicated at block 118.

Steps 121 through 134 represent a fall confirmation algorithm 120 performed in response to a preliminary fall detection. The low sample rate signal analysis of the 3D accelerometer signal used for making a preliminary detection reduces processing time and power required for detecting that the patient has fallen. Analysis of the high frequency components of the 3D accelerometer signal and additional analysis of the low sample rate signal is performed only after a preliminary detection is made based on the low sampling rate data.

Inputs to the fall confirmation algorithm 120 include the digitized 3D accelerometer signal previously stored at block 102, the reference vector computed at block 106, the low frequency sampled data from block 108, and angle $\Theta(0)$ computed at block 112, determined to be cross the fall detection threshold.

An analysis window is set at block 121 relative to the time of the fall threshold crossing by angle $\Theta(0)$. The fall confirmation algorithm 120 is performed to analyze the 3D accelerometer signal during this analysis window. In one embodiment, a three-second analysis window is defined beginning two low sample rate signal points prior to the angle $\Theta(0)$ greater than the fall threshold angle and ending one low sample rate signal point after angle $\Theta(0)$. In the illustrative embodiment, the analysis window will be three seconds long when a one sample per second sample rate is used. Longer or shorter analysis windows may be defined, however, and the analysis window length will depend in part on the low frequency sampling rate of the data and number of data points to be analyzed. The analysis window may correspond to the time interval X for which data is stored at block 102.

At block 122, acceleration magnitudes, computed as the Euclidean Norm in one embodiment, of the digitized 3D accelerometer signal is computed for the digitized signal. The magnitude may be computed for each digitized data point during the analysis window or a subset of high sampling rate data points during the analysis window.

The output of block 122 is provided as input to a band pass filter at block 124. Acceleration measurements performed by the inventors of the instant application reveal that accelerometer signal corresponding to normal patient daily activities typically falls within a range of 0 to 25 Hz. Accelerometer signals during a fall typically range up to about 50 Hz. As such, examination of accelerometer signal up to at least 50 Hz is performed in one embodiment. Band pass filtering of the 3D accelerometer signal between 1 Hz and 50 Hz filters the static component, i.e. gravity, and noise, so that the computed vector magnitudes correspond to the high frequency accelerations of the patient. It is noted that the lower limit of the band pass filter may be less than or greater than 1 Hz for effectively removing the static component of the 3D accelerometer signal.

At block 126, the magnitudes computed at block 122 for the high sample rate signal points selected over the analysis window are compared to an impact threshold. In one embodiment, the impact threshold is selected to correspond to a high acceleration signal that occurs upon impact with a surface such as the floor or ground (or another obstacle that may be present between the patient and the floor or ground). The acceleration magnitude reached at impact will be greater than the acceleration experienced by the accelerometer while the patient is falling. As such, in one embodiment the comparison at block 126 is particularly directed to detecting an acceleration corresponding to impact for detecting that the patient has fallen in contrast to detecting an acceleration magnitude corresponding to movement of the patient through the air as the patient is falling, prior to striking a surface. In one embodiment, the impact threshold is set at approximately 3 g but may be set to values greater or less than this value. If a high acceleration exceeding the impact threshold is not detected, a fall is not detected at block 140. Though not specifically shown in FIG. 5, after completing the high sample rate signal analysis of the accelerometer signal, ambulatory monitoring for a patient fall may continue by returning to block 102 to allow continuous monitoring for fall detection.

As will be described below, an additional or alternative analysis of the magnitudes of the high frequency components of the 3D accelerometer signal may include searching for a signal magnitude less than a falling threshold, e.g. less than 1 g. When the patient is falling, the accelerometer will experience an acceleration of less than 1 g just before impact. Detection of this low magnitude acceleration may be used to confirm that a patient has fallen.

At block 128, the low sample rate signal, received as input from block 108, is used to compute at least one angle between the reference vector and a position vector occurring prior to the angle $\Theta(0)$. In one embodiment, two angles occurring prior to angle $\Theta(0)$ are computed. Angle $\Theta(-1)$ is computed and refers to the angle between the reference vector and the 3D accelerometer signal vector one low sample rate signal point earlier than angle $\Theta(0)$. Angle $\Theta(-2)$ refers to the angle between the reference vector and the 3D accelerometer signal vector two low sample rate signal points earlier than angle $\Theta(0)$. For a 1 sample per second sampling rate, angle $\Theta(-1)$ and angle $\Theta(-2)$ occur one second earlier and two seconds earlier, respectively, than angle $\Theta(0)$. It is recognized that the computation of one or more angles computed prior to angle $\Theta(0)$ is not limited to using low sample rate signal points obtained at block 108 but could alternatively use one or more sample points selected from the high sample rate signal stored at block 102.

The angle(s) computed for 3D accelerometer signal sample points occurring earlier than the fall threshold crossing are compared to an upright threshold for verifying that prior to the fall threshold crossing the patient was in a substantially upright position, from which a fall could have occurred. An angle $\Theta(-N)$, occurring prior to detecting the fall threshold crossing, is compared to the upright threshold, for example 30 degrees at block 132. As described above, a computed angle $\Theta$ is the difference between the instantaneous 3D accelerometer vector and the stored reference vector corresponding to an upright position. As such, if an angle $\Theta(-N)$ prior to detecting the fall threshold crossing is less than approximately thirty degrees, or another selected upright threshold angle, the patient is detected as being in a substantially upright position prior to the fall threshold crossing.

At block 130, one or more angles $\Theta(+N)$ are computed using sample points occurring after detecting the fall threshold crossing. The one or more angles angle $\Theta(+N)$ are compared to a non-upright threshold, for example 60 degrees. In one embodiment, an angle $\Theta(+1)$ refers to the angle between the reference vector and the vector at one sample point after the fall threshold crossing (angle $\Theta(0)$). Using a 1 Hz sampling rate, angle $\Theta(+1)$ occurs one second after angle $\Theta(0)$. If the angle $\Theta(+1)$ is greater than approximately sixty degrees, or another selected non-upright threshold angle, the patient is detected as being in a non-upright position after the preliminary fall detection.

If a substantially upright position is confirmed prior to the fall threshold crossing and a non-upright position is confirmed after the fall threshold crossing, with both the upright and non-upright position detections occurring within the analysis window, the fall confirmation criteria are met at block 132. The preliminary fall detection is confirmed at block 142 based on the fall verification criteria being met and the impact threshold crossing of the acceleration signal magnitude.

Alternatively, a difference between an angle $\Theta(-N)$, occurring prior to the fall threshold crossing, and an angle $\Theta(+M)$, occurring after the fall threshold crossing, this difference referred to as Delta(Θ(−N), Θ(+M)), where N and M may or may not be equal, may be compared to a fall confirmation threshold at block 132. For example, if the difference in angles Θ(−1) and Θ(+1) is greater than a fall confirmation threshold, e.g. thirty degrees, the preliminary detection that the patient has fallen is confirmed at block 142, based also on the acceleration magnitude crossing the impact threshold.

At block 134 additional fall verification criteria may be evaluated. For example, other physiological signals such as patient activity and the ECG (current heart rhythm) may optionally be analyzed to support the fall detection. A patient activity signal can be obtained from the accelerometer signal. In some embodiments, a low patient activity level corroborates the accelerometer position and magnitude data that a patient has fallen. However, in some cases, patient movement after a fall may still be present making the activity signal unreliable in some instances.

A response to the detected fall is provided at block 144. The response at block 144 may be physiological signal data storage, generating a medical alert, initiating or adjusting a therapy delivered by the IMD, or initiating a transfer of data from the IMD to an external device or a remote patient monitoring center.

Figure 6:
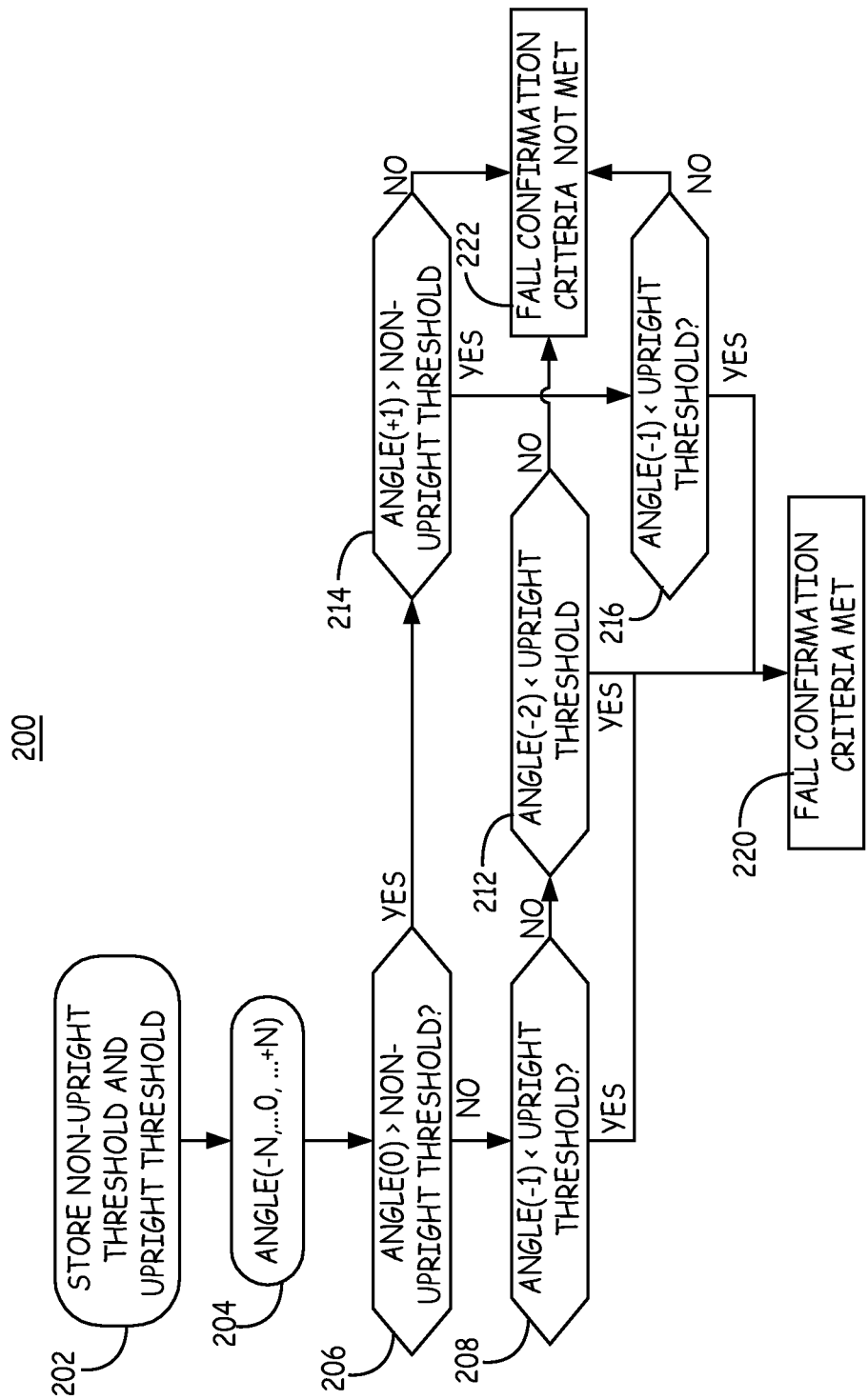
FIG. 6 is a flow chart of a method for determining if fall verification criteria are met according to an alternative embodiment.

FIG. 6 is a flow chart of a method for determining if fall verification criteria are met according to an alternative embodiment of the invention. Method 200 is performed at block 132 of method 100 in one embodiment of the invention for confirming a preliminary fall detection based on patient position data before and after a preliminary fall detection. More specifically, method 200 is performed to verify that the patient was in a substantially upright position prior to the preliminary fall detection and in a substantially non-upright position after the preliminary fall detection. A substantially upright position is detected as a position that results in an angle Θ less than an upright threshold; the upright threshold defined as approximately thirty degrees in one embodiment. A substantially non-upright position is detected as a position that results in an angle Θ greater than a non-upright threshold; the non-upright threshold defined as approximately sixty degrees in one embodiment.

At block 202 the upright and non-upright thresholds are stored. These threshold values may be fixed values or programmable by a clinician. In one embodiment, the non-upright threshold is greater than the fall threshold and the upright threshold is less than the fall threshold. At block 204 the computed angles Θ(−N, ... 0, ... +M), wherein N and M may or may not be equal are provided as input for method 200. In one embodiment, the computed angles include angle Θ(−2), angle Θ(−1), angle Θ(0), and angle Θ(+1). Angle Θ(0) is the first angle to cross the fall threshold and is defined to occur at time 0. Angle Θ(−2), angle Θ(−1), angle Θ(+1) correspond to angles computed for sample points relative to time 0.

At block 206, angle Θ(0) is compared first to the non-upright threshold. At block 208, angle Θ(−1) is compared to the upright threshold. If angle Θ(0) exceeds the non-upright threshold and angle Θ(−1) is less than the upright threshold, the fall confirmation criteria are met for confirming a preliminary fall detection in combination with acceleration magnitude criteria.

If angle Θ(0) is not greater than the non-upright threshold (block 206) but angle Θ(+1) is greater than the non-upright threshold (block 214) and angle Θ(−1) is less than the upright threshold (block 216), the fall confirmation criteria are met at block 220.

If the angle Θ(0) is greater than the non-upright threshold (block 206) and the angle Θ(−1) is not less than the upright threshold (block 208), but the angle Θ(−2) is less than the upright threshold (block 212), the fall confirmation criteria are met at block 220 for use in conjunction with acceleration magnitude analysis for confirming a preliminary fall detection.

The operation of method 200 verifies that a change in the angle Θ that is at least the difference between an upright threshold and a non-upright threshold occurs within a maximum period of time. If this condition is not satisfied, the fall confirmation criteria are not met at block 222. In one embodiment, a change in the angle Θ of at least thirty degrees (from less than the upright threshold to greater than the non-upright threshold) must occur within two seconds for the fall to be confirmed. The timeframe in which the change in the angle Θ(0) is evaluated will depend in part on sampling rates. If a shorter timeframe for verifying the position change corresponding to a fall is desired, a sampling rate of higher than 1 sample per second could be used or sample points for computing the angles may be selected from the high sample rate signal. In selecting a low sampling rate and an analysis window it is generally desirable to minimize the time for detecting that the patient has fallen, for example within 1-2 seconds after the fall.

Figure 7:
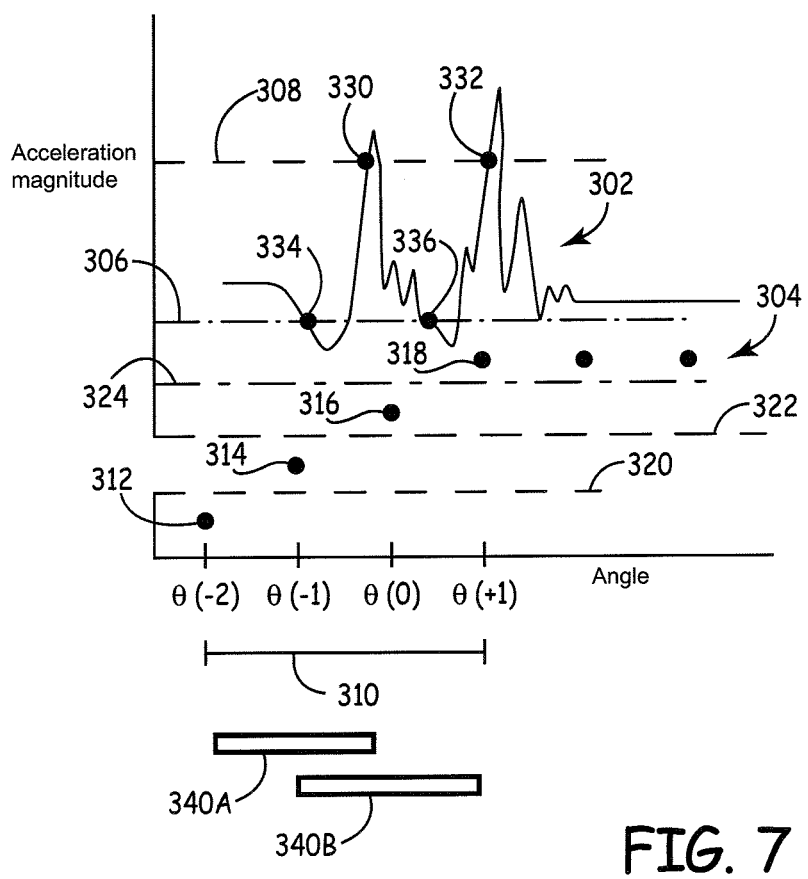
FIG. 7 is plot of an acceleration signal and computed angles $\ominus$ over an analysis window.

FIG. 7 is plot of an acceleration signal 302 and computed angles Θ 304 over an analysis window 310. The first sample point 316 of angle Θ to cross a fall threshold 322 is defined as angle Θ(0). Analysis window 310 is defined to extend two low sample rate signal points earlier than angle Θ(0) and one sample point later, i.e., from angle Θ(−2) to angle Θ(+1). A moving maximum time interval 340A and 340B, "340" hereafter, is used to determine if a change in angle Θ meets fall confirmation criteria within analysis window 310. A rapid change in angle Θ, for example in less than two seconds, from less than the upright threshold 320 to greater than the non-upright threshold 324, indicates that the patient has most likely fallen. A change in angle Θ(0) from less than the upright threshold 320 to greater than the non-upright threshold 324 over a time interval that is greater than the maximum time interval 340 is more likely associated with an intentional position change by the patient, not a fall. The maximum time interval 340 for detecting the change in angle Θ may be equal to or less than the analysis window 310. When the maximum time interval 340 is less than the analysis window 310, the maximum time interval 340 is a moving window that includes the angle Θ(0) and at least one preceding angle Θ (interval 340A) or at least one succeeding angle Θ (interval 340B).

In the example shown, angle Θ(−1) 314 is greater than an upright threshold 320. Angle Θ(−2) 312 is less than an upright threshold 320. Angle Θ(+1) 318 is greater than a non-upright threshold 324. Even though the angle Θ is increasing over the analysis window 310, the change in angle Θ from less than the upright threshold 312 to greater than the non-upright threshold 324 does not occur within the maximum time interval 340. In other words, the difference between any two of the angles Θ(−2), Θ(−1), Θ(0), and Θ(+1) does not exceed the difference between the upright threshold 320 and the non-upright threshold 324 within the maximum time interval 340. Therefore, a preliminary fall detection based on sample point 316 crossing the fall threshold 322 is not confirmed according to the example shown and the illustrative embodiment.

The acceleration magnitude signal 302 crosses an impact threshold 308 twice at points 330 and 332 within the analysis window 310. The magnitude criteria for confirming a preliminary fall detection is met but the fall confirmation criteria relating to the change in angle Θ are not met. No fall would be detected in the example shown in FIG. 7 according to the illustrative embodiment of FIGS. 5 and 6.

In some embodiments, a "falling" threshold 306 is defined to detect an acceleration magnitude of less than 1 g experienced by the accelerometer when the patient is falling, just prior to impact with a surface. The falling threshold 306 is crossed at points 334 and 336. Only the first threshold crossing at 334 need be detected for use in detecting that the patient has fallen. The "double" crossing of the falling threshold 306 at points 334 and 336 and the impact threshold 308 at points 330 and 332 may correspond to a bounce or double strike with one or more surfaces during the fall. The falling threshold 306 may be used in addition to or alternatively to the impact threshold 308 for determining if acceleration magnitude criteria are met for confirming a preliminary fall detection.

Thus, a method and associated apparatus for detecting if a patient has fallen have been presented in the foregoing description with reference to specific embodiments. It is appreciated that various modifications to the referenced embodiments may be made without departing from the scope of the invention as set forth in the following claims.

The invention claimed is:

1. A medical device comprising:
    a physiological sensor for sensing a signal in a patient;
    a three-axis accelerometer for generating a 3D accelerometer signal; and
    a processor configured to:
        compute a reference vector corresponding to an upright patient position based on the 3D accelerometer signal;
        determine a current patient position vector based, at least in part, on the 3D accelerometer signal sampled at a low sample rate;
        determine that a difference between the current patient position vector and the reference vector exceeds a difference threshold;
        in response to the determination that the difference exceeds the difference threshold, determine an acceleration magnitude based, at least in part, on the 3D accelerometer signal sampled at a high sample rate being higher than the low sample rate; and
        detect that the patient has fallen based, at least in part, on the patient position and the acceleration magnitude.

2. The device of claim 1 wherein the processor is further configured to:
    compute a current angle between the reference vector and the current patient position vector; and
    compare the computed current angle to a first threshold angle to determine that a difference between the current patient position vector and the reference vector exceeds the difference threshold.

3. The device of claim 1 wherein the low sample rate is not more than approximately one sample per second.

4. The device of claim 1 wherein, in response to the determination that the difference between the current patient position vector and the reference vector exceeds the difference threshold, the processor is further configured to:
    set an analysis window of the 3D accelerometer signal sampled at the high sample rate, the analysis window set relative to a time at which the difference between the current patient position vector and the reference vector exceeds the difference threshold; and
    determine a plurality of acceleration magnitudes of the 3D accelerometer signal sampled at the high sample rate within the analysis window, and
    wherein the processor is configured to detect the patient fall based on at least one of the acceleration magnitudes crossing a predetermined magnitude threshold within the analysis window.

5. The device of claim 4 wherein, to determine each of the plurality of acceleration magnitudes of the 3D accelerometer signal sampled at the high same rate within the analysis window, the processor is configured to:
    determine a three-dimensional position vector for each sample of the 3D accelerometer signal sampled at a high sample rate within the analysis window; and
    determine a Euclidean norm of the three-dimensional position vector as the acceleration magnitude.

6. The device of claim 4 wherein the processor is configured to set the analysis window to begin at least two low sample rate signal points prior to the time at which the difference between the current patient position vector and the reference vector exceeds the difference threshold and end at least one low sample rate signal point after the time at which the difference between the current patient position vector and the reference vector exceeds the difference threshold.

7. The device of claim 3 wherein the high sample rate is approximately two hundred fifty-six samples per second.

8. The device of claim 4 wherein, in response to one of the acceleration magnitudes crossing the predetermined magnitude threshold, the processor is further configured to:
    determine a prior patient position vector occurring prior to the current patient position vector; and
    determine a prior angle between the prior patient position vector and the reference vector,
    wherein the processor is configured to detect the patient fall based on at least one of the acceleration magnitudes crossing a predetermined magnitude threshold within the analysis window and the prior angle.

9. The device of claim 4 wherein, in response to one of the acceleration magnitudes crossing the predetermined magnitude threshold, the processor is further configured to:
    determine a subsequent patient position vector occurring after the current patient position vector; and
    determine a subsequent angle between the subsequent patient position vector and the reference vector,
    wherein the processor is configured to detect the patient fall based on at least one of the acceleration magnitudes crossing a predetermined magnitude threshold within the analysis window and the subsequent angle.

* * * * *

UNITED STATES PATENT AND TRADEMARK OFFICE
CERTIFICATE OF CORRECTION

| | | |
|---|---|---|
| PATENT NO. | : 8,814,811 B2 | Page 1 of 1 |
| APPLICATION NO. | : 12/126084 | |
| DATED | : August 26, 2014 | |
| INVENTOR(S) | : Patrick Scholten and Harry Bernardus Antonius Kerver | |

It is certified that error appears in the above-identified patent and that said Letters Patent is hereby corrected as shown below:

In the Claims

Claim 5, Column 12, line 16, delete "... sampled at the high same rate within the ..." and insert in place thereof --"... sampled at the high sample rate within the ..."--

Signed and Sealed this
Seventeenth Day of March, 2015

Michelle K. Lee
*Director of the United States Patent and Trademark Office*